US010857123B2

(12) United States Patent
Hacini-Rachinel

(10) Patent No.: US 10,857,123 B2
(45) Date of Patent: Dec. 8, 2020

(54) NLRP3 INHIBITORS FOR THE TREATMENT OF INFLAMMATORY SKIN DISORDERS

(71) Applicant: GALDERMA RESEARCH & DEVELOPMENT, Biot (FR)

(72) Inventor: Feriel Hacini-Rachinel, Biot (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 16/072,686

(22) PCT Filed: Jan. 25, 2017

(86) PCT No.: PCT/FR2017/050160
§ 371 (c)(1),
(2) Date: Mar. 4, 2019

(87) PCT Pub. No.: WO2017/129897
PCT Pub. Date: Aug. 3, 2017

(65) Prior Publication Data
US 2019/0192478 A1      Jun. 27, 2019

(30) Foreign Application Priority Data

Jan. 25, 2016   (FR) ...................................... 16 50555

(51) Int. Cl.
| | | |
|---|---|---|
| *A61K 31/341* | (2006.01) | |
| *A61P 17/04* | (2006.01) | |
| *A61P 17/06* | (2006.01) | |
| *A61K 9/00* | (2006.01) | |
| *A61K 31/381* | (2006.01) | |
| *A61K 31/4184* | (2006.01) | |
| *A61K 31/18* | (2006.01) | |
| *A61K 31/473* | (2006.01) | |
| *A61K 31/357* | (2006.01) | |
| *A61K 31/404* | (2006.01) | |

(52) U.S. Cl.
CPC .......... *A61K 31/341* (2013.01); *A61K 9/0014* (2013.01); *A61K 31/18* (2013.01); *A61K 31/357* (2013.01); *A61K 31/381* (2013.01); *A61K 31/404* (2013.01); *A61K 31/4184* (2013.01); *A61K 31/473* (2013.01); *A61P 17/04* (2018.01); *A61P 17/06* (2018.01)

(58) Field of Classification Search
None
See application file for complete search history.

(56) References Cited

U.S. PATENT DOCUMENTS

| | | | |
|---|---|---|---|
| 2009/0137569 A1 | 5/2009 | Biadatti et al. | |
| 2018/0044287 A1* | 2/2018 | O'Neill | ................ C07D 403/12 |
| 2019/0119203 A1* | 4/2019 | Glick | .................... C07C 317/22 |

FOREIGN PATENT DOCUMENTS

| | | |
|---|---|---|
| FR | 2898497 | 9/2007 |
| WO | 98/32733 | 7/1998 |

OTHER PUBLICATIONS

Shao et al., NLRP3 inflammasome and its inhibitors: a review. Frontiers in Pharmacology, 2015, 6, 1-9.*
Schafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
Sa et al., Inflammasomes and dermatology. Anais Brasileiros de Dermatologia, 2016, 91, 566-578.*
International Search Report and Written Opinion of the International Searching Authority dated Apr. 12, 2017 corresponding to International Patent Application No. PCT/FR2017/050160, 11 pages.
Coll, Rebecca C. et al., "A small-molecule inhibitor of the NLRP3 inflammasome for the treatment of inflammatory diseases", Nature Medicine, vol. 21, pp. 248-255 (2015).
Berge, Stephen M. et al., "Pharmaceutical Salts," Journal of Pharmaceutical Sciences, vol. 66, No. 1, pp. 1-19, (1977).

* cited by examiner

*Primary Examiner* — Po-Chih Chen
(74) *Attorney, Agent, or Firm* — Foley & Lardner LLP; Sunit Talapatra

(57) ABSTRACT

The use of an NLRP3 inhibitor compound is described in the treatment of inflammatory skin disorders, in particular psoriasis and atopic dermatitis.

18 Claims, 2 Drawing Sheets

NLRP3 INHIBITORS FOR THE TREATMENT OF INFLAMMATORY SKIN DISORDERS

CROSS-REFERENCE TO PRIOR APPLICATIONS

Figure 1:
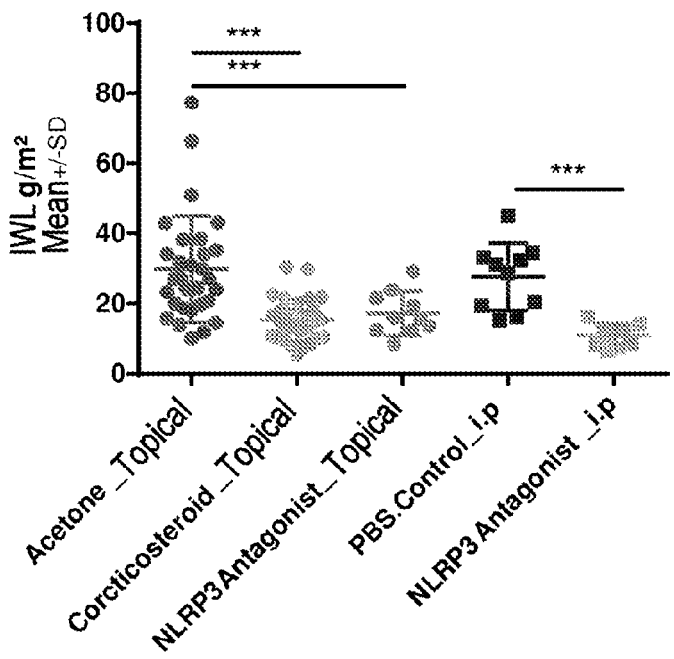

This application is the U.S. National Stage of PCT/FR2017/050160, filed Jan. 25, 2017, (published in the French language on Aug. 3, 2017 as WO 2017/129897 A1; the title and abstract were also published in English), which claims priority under 35 U.S.C. § 119 of French Patent Application No. FR 1650555, filed Jan. 25, 2016, each assigned to the assignee hereof.

The present invention relates to the field of therapeutics and more particularly relates to NLRP3 receptor inhibitor compounds used in the treatment and/or prevention of inflammatory skin disorders.

TECHNICAL BACKGROUND OF THE INVENTION

Inflammatory skin disorders are skin disorders accompanied by an inflammatory component. There are various types of inflammatory skin disorders categorized according to their location, their causes and their symptoms. They are very common skin disorders and it can sometimes be difficult to diagnose them. This is because the immune system in the skin has limited possibilities for response to internal and external stimuli and thus a very large number of skin disorders have an inflammatory profile and exhibit only a very small number of specific pathological characteristics.

Among inflammatory skin disorders, atopic dermatitis, a chronic inflammatory disease which affects the skin, manifests itself through itching, dryness and skin lesions. Atopic dermatitis most commonly appears during early childhood and can persist or begin in adulthood. This condition is characterized by an inappropriate response of the immune system directed against environmental antigens, known as allergens. In the majority of cases, acarids are responsible for the allergic reaction.

The cause of atopic dermatitis is multifactorial, with complex interactions between genetic factors and the environment. Indeed, even though in 30% of cases atopic dermatitis is associated with a mutation in the filaggrin gene, the large increase in the incidence of the disease over the past 30 years in industrialized countries cannot in any way be explained by genetics, indicating the fundamental role played by the environment. In accordance with this hypothesis, many epidemiological studies show that individuals raised in a rural environment develop fewer allergic diseases, including atopic dermatitis, than individuals living in industrialized areas. Allergic individuals have a predisposition to the development of type E immunoglobulins (IgE), directly responsible for the first symptoms of the allergy; they are termed "atopic".

Atopic dermatitis is described as the initial step of the "atopic march" which, in more than 40% of cases, will lead to the appearance of other allergic diseases, such as allergic rhinitis or allergic asthma.

In terms of histology and immunology, atopic dermatitis is characterized by a thickening of the epidermis and infiltration of the skin by mast cells, helper T lymphocytes, eosinophils and dendritic cells.

It is accepted that the acute phase of this disease is initiated by CD4$^+$ T lymphocytes of Th2 and Th22 type. In the more chronic phases, characterized by lichenified skin lesions, the appearance of other lymphocyte types: Th1 and Th17 is observed.

To date, the available therapies are not entirely satisfactory. This is because most treatments provide temporary and incomplete relief of the symptoms. In addition, the long-term use of topical corticosteroids is subject to side effects such as atrophy or thinning of the skin, and topical inhibitors of calcineurin can cause a local irritation of the skin or burns and itching when the treatment is begun. These side effects can affect observance by the patient or by parents. Finally, systemic and UV therapies must be used with great care and must be reserved for adults with serious cases.

Another inflammatory skin disorder is psoriasis, which is characterized by red plaques, covered with whitish squames which detach from the skin. These plaques are located in particular on the elbows, knees, scalp and lower back, but can also affect other parts of the body. The skin cells multiply rapidly and accumulate in psoriatic plaques. The severity of this disorder can vary. This disorder appears to be multifactorial and can also be worsened by numerous external factors, such as stress, smoking, alcohol, the stopping of corticosteroids, etc. The treatments available to date have a limited efficacy and can only be used over short periods of time. Reference may particularly be made to topical treatments based on corticosteroids, on vitamin D analogs, on retinoids, on fluocinonide, etc. On the other hand, the latter are often not very efficacious, cannot be used over long periods of time, and induce in particular skin irritations and also worsening of the disorder when the treatment is stopped.

Given the complexity of the pathophysiology of skin disorders, such as atopic dermatitis or psoriasis, and also the side effects associated with the available treatments for these inflammatory skin disorders, there is a need to have new compositions that are of use for the treatment and/or prevention of these disorders.

There is in particular a need to have a treatment which has improved efficacy, which has few side effects and which is well tolerated, in particular in young children.

SUMMARY OF THE INVENTION

In this context, the Applicant proposes using compounds which inhibit the NLRP3 receptor belonging to the NOD-like receptor (NLR) family, in particular the compounds of general formula (I), for the treatment and/or prevention of an inflammatory skin disorder and in particular of atopic dermatitis or of psoriasis.

The subject of the present invention thus relates to a compound of general formula (I):

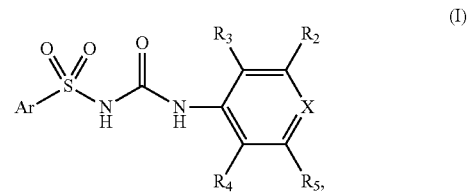

in which:
X represents a group C—R$_1$ or a nitrogen atom;
R$_1$ represents a hydrogen atom or a halogen;
R$_2$, R$_3$, R$_4$ and R$_5$ independently represent a hydrogen atom or a C$_1$-C$_6$ alkyl, R$_2$ and R$_3$ taken together possibly forming a cyclopentyl with the carbon atoms of the phenyl to which they are bonded, and $R_4$ and $R_5$ taken together possibly forming a cyclopentyl with the carbon atoms of the phenyl to which they are bonded; and Ar represents a group chosen from:

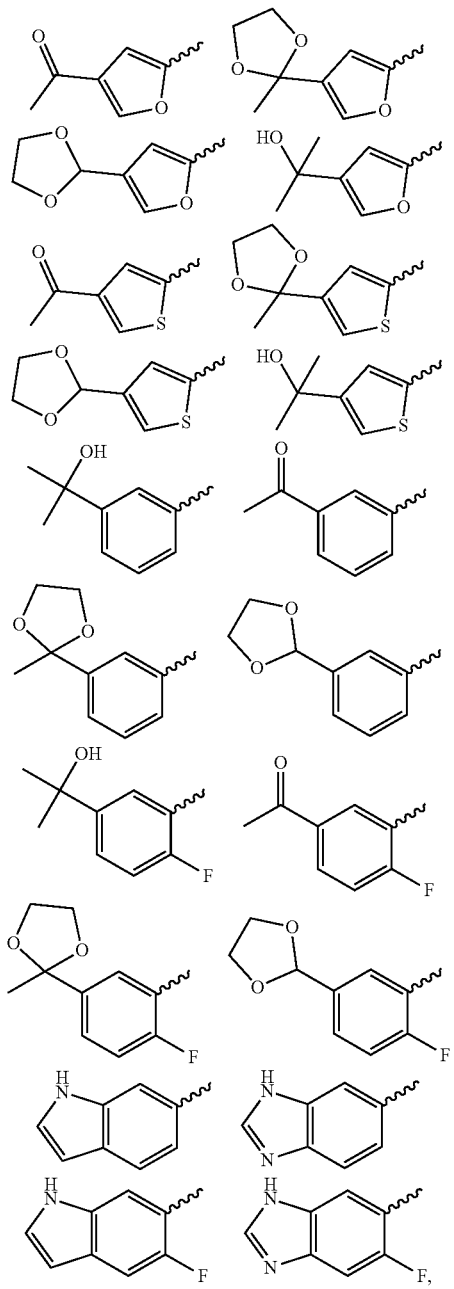

or a pharmaceutically acceptable salt, solvate or hydrate thereof, for use in the treatment and/or prevention of inflammatory skin disorders.

In one preferred embodiment, the compounds as defined herein are used in the treatment and/or prevention of atopic dermatitis or of psoriasis.

Another subject of the invention is a pharmaceutical composition comprising a compound as defined herein, for use in the treatment and/or prevention of an inflammatory skin disorder, preferably atopic dermatitis or psoriasis.

A method for treating an inflammatory skin disorder, comprising the administration of a compound or of a pharmaceutical composition as defined herein in a sufficient amount in a patient suffering from said inflammatory skin disorder is also described.

The invention also relates to the use of a composition as defined herein, for producing a medicament or a pharmaceutical composition intended for preventing or treating an inflammatory skin disorder.

Preferentially, the pharmaceutical composition used in the present invention is intended for topical application.

FIGURE LEGENDS

FIG. 1: Measurement of the insensible water loss at day 51, after topical application of acetone (negative control), of 0.1% betamethasone valerate (corticosteroid, positive control), and of the NLRP3 antagonist compound (compound No. 3, 2% in an acetone carrier), of the PBS system (negative control), and after systemic application of the NLRP3 antagonist compound (compound No. 3, 200 µl, 2.5 mg/ml once a day).

Figure 2:
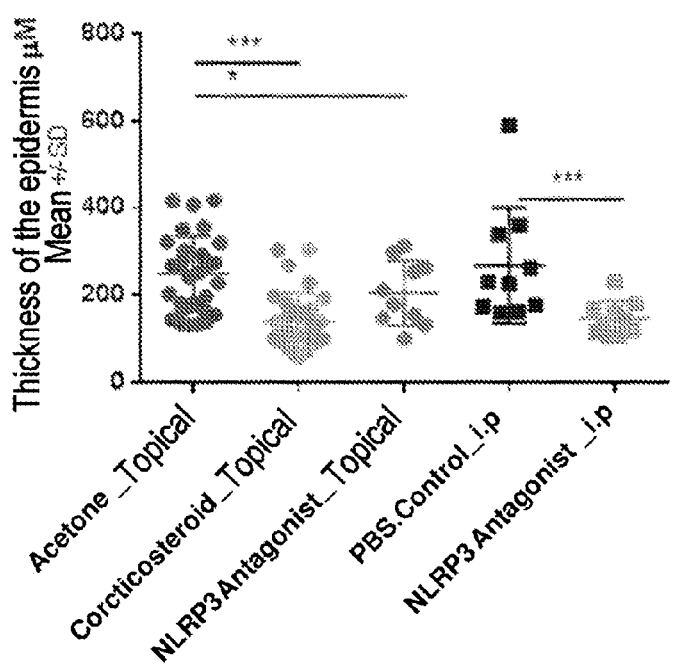

FIG. 2: Measurement of the thickness of the epidermis at day 51, after topical application of acetone (negative control), of 0.1% betamethasone valerate (topical corticosteroid, positive control), and of the NLRP3 antagonist compound (compound No. 3, 2% in an acetone carrier), of the PBS system (negative control), and after systemic application of the NLRP3 antagonist compound (compound No. 3, 200 µl, 2.5 mg/ml once a day).

Figure 3:
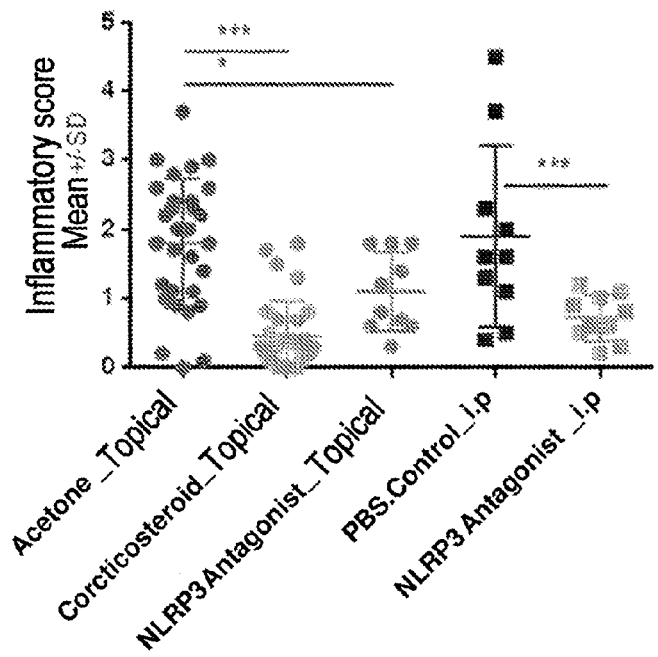

FIG. 3: Measurement of the inflammatory score at day 51, after topical application of acetone (negative control), of 0.1% betamethasone valerate (topical corticosteroid, positive control), and of the NLRP3 antagonist compound (compound No. 3, 2% in an acetone carrier), of the PBS system (negative control), and after systemic application of the NLRP3 antagonist compound (compound No. 3, 200 µl, 2.5 mg/ml once a day).

Figure 4:
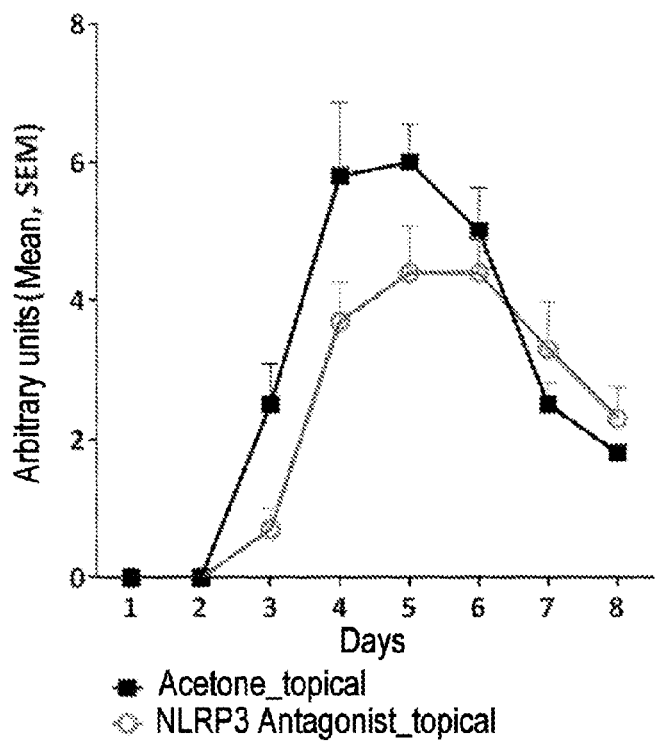

FIG. 4: Measurement of the kinetics of the clinical score from day 1 to day 8 after topical application of 3% of the NLRP3 antagonist compound (compound No. 3) dissolved in acetone, or acetone alone (negative control).

DETAILED DESCRIPTION OF THE INVENTION

Definitions

For the purposes of the present invention, the term "inflammatory skin disorders" refers to any skin disorder accompanied by an inflammatory component. The term includes in particular rosacea, acne, eczema, hand eczema, urticaria, facial and pudic erythema, pruritus, atopic dermatitis and psoriasis in all its forms, such as cutaneous, mucosal or nail psoriasis, or psoriatic arthritis.

The term "NLRP3 receptor" denotes the protein "NOD-like receptor family, pyrin domain containing 3", which is the most studied receptor of the NLR receptor family. NLRP3 is involved in the formation of a complex called the "inflammasome" after having detected a ligand. This inflammasome cleaves and thus activates caspase-1 which in turn can initiate the maturation of interleukin 1β (IL-1β) and of IL-18 by cleaving their inactive precursors. The activation of these interleukins makes it possible to activate the cell death inflammatory pathway, called pyroptosis.

Two steps are required for the NLRP3 activation mechanism:
- the first is a step of form recognition inducing the production of the pro-form of IL1β and of NLRP3,
- the second step consists of the assembly and of the activation of the molecular complex which is the inflammasome, induced by various ligands.

NLRP3 is involved in the genesis of numerous complex disorders, in particular with regard to metabolic disorders such as type II diabetes, atherosclerosis or else obesity. It appears that NLRP3 is also involved in pulmonary disorders, but also hepatic or renal disorders, or else age-related disorders.

For the purposes of the present invention, the term "NLRP3 inhibitor compounds" is intended to mean any compound capable of inhibiting the activation of the inflammasome via the NLRP3 receptor belonging to the NOD-like receptor (NLR) family. More particularly, the compounds according to the present invention are capable of inhibiting the activation of the inflammasome via NLRP3 through the inhibition of the activation of IL1β via the caspase 1 pathway, but also of inhibiting the canonical and non-canonical activation of the inflammasome via the NLRP3 receptor. More particularly, the compounds of use according to the present invention are capable of specifically inhibiting the NLRP3 receptor without inhibiting the activation of other components of the inflammasome. Many NLRP3 inhibitor compounds are known. The company Pfizer has thus previously developed several compounds of the substituted sulfonyl urea derivative type, having a significant inhibitory activity on the activation of IL1α and β, in particular through the specific inhibition of NLRP3.

In one embodiment, the term "treatment" or "treating" denotes an improvement, prophylaxis, or reversion of a disease or of an ailment, or at least of a symptom thereof that can be discerned. In another embodiment, the term "treatment" or "treating" denotes an improvement, the prophylaxis, or the reversion of at least one measurable physical parameter associated with the disease or with the disorder being treated, which is not necessarily discernible in or by the subject treated. In another additional embodiment, the term "treatment" or "treating" denotes the inhibition or slowing down of the progression of a disease or an ailment, physically, for example the stabilization of a symptom which is discernible, physiologically, for example the stabilization of a physical parameter, or both. In another embodiment, the term "treatment" or "treating" denotes delaying the appearance of a disease or ailment.

In some embodiments, the compounds are administered as a preventive measure. In the present context, this preventive measure denotes a reduction in the risk of acquiring a specified disease or ailment, but also a reduction, an inhibition or a slowing down of the appearance of the symptoms associated with this disease. When the disease is atopic dermatitis, characteristic symptoms are, for example, itching, dryness or skin lesions. When the disease is psoriasis, characteristic symptoms are for psoriasis red plaques, covered with whitish squames which detach from the skin.

For the purposes of the present invention, the term "subject" and/or "patient" is intended to mean any mammal, and more particularly human beings, men, women or children. According to another particular aspect of the invention, the term "subject" and/or "patient" is preferably intended to mean pregnant women, children and infants.

NLRP3 Inhibitors

The compounds used in the context of the present invention correspond to general formula (I):

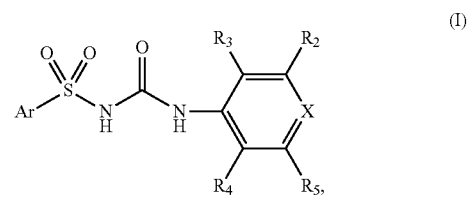

in which:
X represents a group C—$R_1$ or a nitrogen atom;
$R_1$ represents a hydrogen atom or a halogen;
$R_2$, $R_3$, $R_4$ and $R_5$ independently represent a hydrogen atom or a $C_1$-$C_6$ alkyl, $R_2$ and $R_3$ taken together possibly forming a cyclopentyl with the carbon atoms of the phenyl to which they are bonded, and $R_4$ and $R_5$ taken together possibly forming a cyclopentyl with the carbon atoms of the phenyl to which they are bonded; and Ar represents a group chosen from:

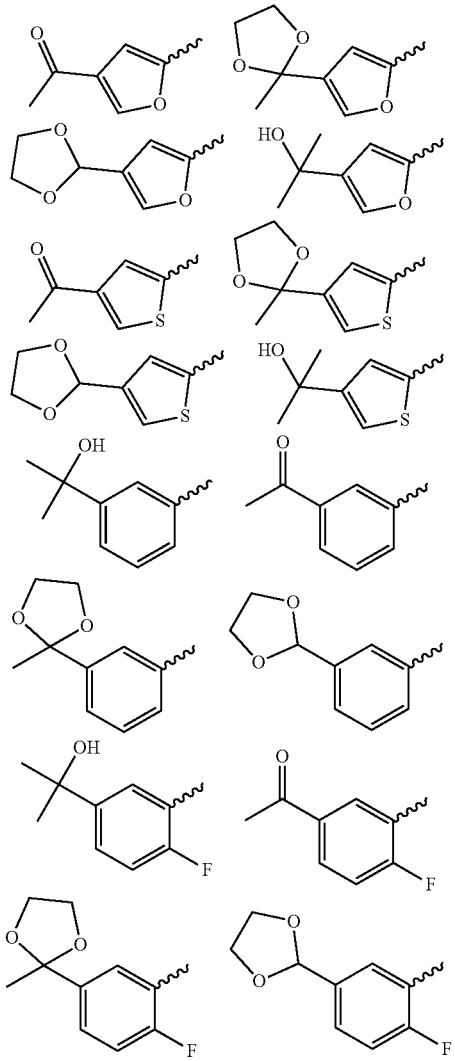

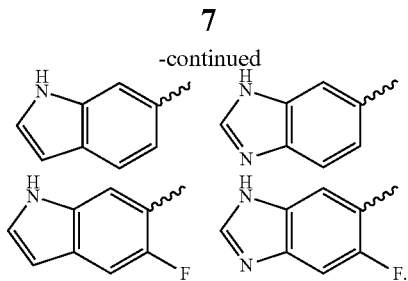

In the context of the present invention, the terms below have the following meanings:

The term "alkyl" represents a linear or branched, saturated aliphatic group typically having from 1 to 18 carbon atoms, from 1 to 10 carbon atoms, preferably from 1 to 6 carbon atoms and even more preferentially from 1 to 4 carbon atoms. As alkyl group having from 1 to 10 carbon atoms, mention may for example be made of methyl, ethyl, isopropyl, butyl, tert-butyl, hexyl, nonyl and dodecyl groups. The alkyl groups having from 1 to 6 carbon atoms ($C_1$-$C_6$ alkyl) are, for example, methyl, ethyl, isopropyl, butyl, tert-butyl and hexyl groups.

The term "cycloalkyl" corresponds to an alkyl group as defined above, linked by a bond at its two ends. Mention may for example be made of cyclopropyl, cyclobutyl, cyclopentyl and cyclohexyl as cycloalkyl having from 3 to 6 carbon atoms.

The term "halogen" corresponds to a fluorine, chlorine, bromine or iodine atom.

The term "Ar" or "aryl" corresponds to a mono or bi-cycle having from 6 to 12 carbon atoms, of formula $C_nH_{(n-2)}$. Mention may for example be made of phenyl, biphenyl or naphthyl groups. In the context of the present invention, the term "Ar" or "aryl" also includes optionally substituted heteroaryls, i.e. aryls comprising at least one heteroatom such as an oxygen, sulfur or nitrogen atom which may be substituted with various substituents. For example, the term "Ar" or "aryl" represents a group chosen from:

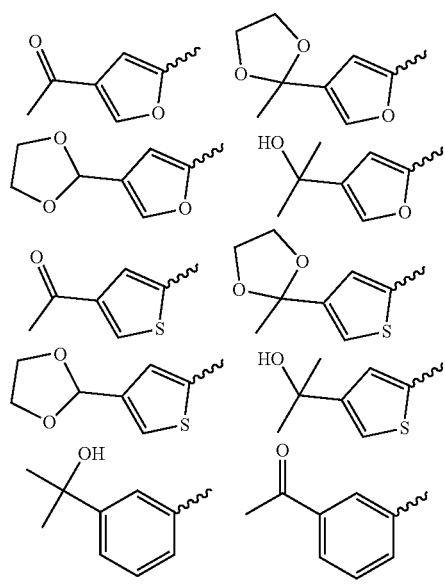

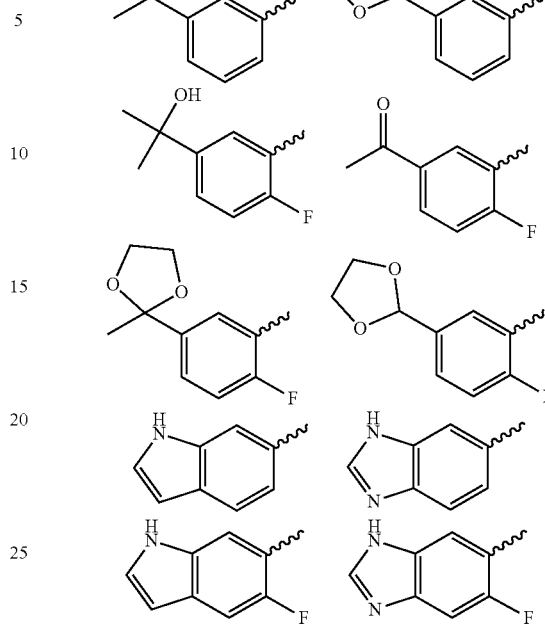

The compounds used in the invention also comprise the pharmaceutically acceptable salts, solvates and hydrates of these compounds.

The expression "pharmaceutically acceptable salt(s)" denotes the salts of a compound of interest which possess the desired biological activity. The pharmaceutically acceptable salts comprise salts of acid or basic groups present in the specified compounds. The pharmaceutically acceptable acid addition salts comprise, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e. 1,1'-methylene-bis-(2-hydroxy-3-naphthoate)) salts. Suitable base salts comprise, but are not limited to, aluminum, calcium, lithium, magnesium, potassium, sodium, zinc, and diethanolamine salts. A list of pharmaceutically acceptable salts is in particular published in the review by Berge et al. (J. Pharm. Sci., 1977, 66(1), 1-19).

The hydrates correspond to a combination of a compound of formula (I) with one or more water molecules.

The solvates correspond to an association of a compound of formula (I) and of a solvent resulting from the fixing of this solvent on the crystals of compound of general formula (I) formed in the presence of this solvent.

In a first particular embodiment, the compounds used in the invention correspond to general formula (I) in which:

X represents a group C—$R_1$ or a nitrogen atom, $R_1$ representing a hydrogen atom or a halogen, preferably a chlorine or fluorine;

$R_2$ and $R_3$ taken together forming a cyclopentyl with the carbon atoms of the phenyl to which they are bonded; and $R_4$ and $R_5$ taken together possibly forming a cyclopentyl with the carbon atoms of the phenyl to which they are bonded.

The compounds according to this particular embodiment correspond to general formula (II):

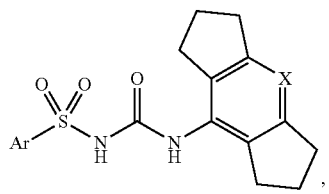
(II)

in which:

X represents a group C—$R_1$ or a nitrogen atom, $R_1$ representing a hydrogen atom or a halogen, preferably a chlorine or fluorine; and Ar represents a group chosen from:

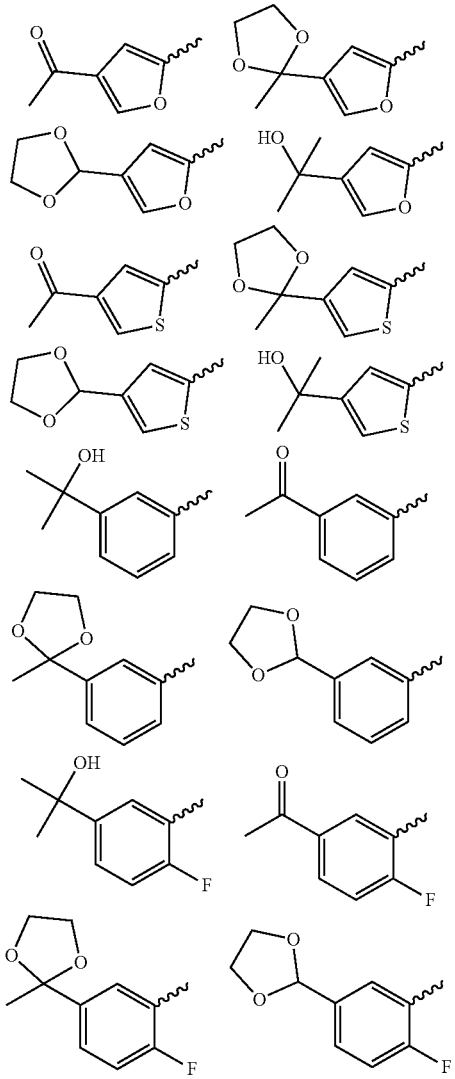

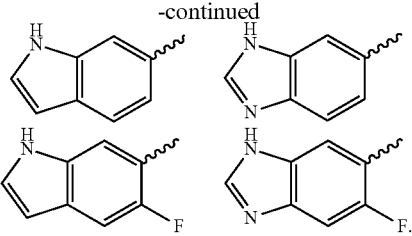

In a second particular embodiment, the compounds used in the invention correspond to general formula (I) in which:

X represents a group C—$R_1$ or a nitrogen atom, $R_1$ representing a hydrogen atom or a halogen, preferably a chlorine or fluorine;

$R_2$ and $R_5$ represent a hydrogen atom; and $R_3$ and $R_4$ represent an isopropyl.

The compounds according to this particular embodiment correspond to general formula (III):

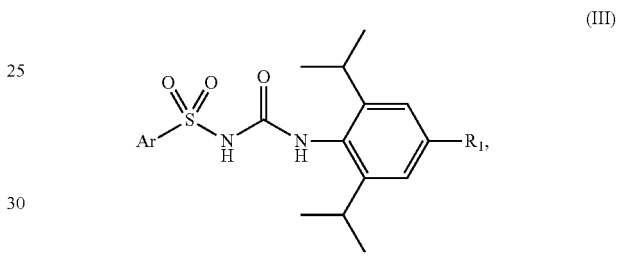
(III)

in which:

$R_1$ represents a hydrogen atom or a halogen; and

Ar represents a group chosen from:

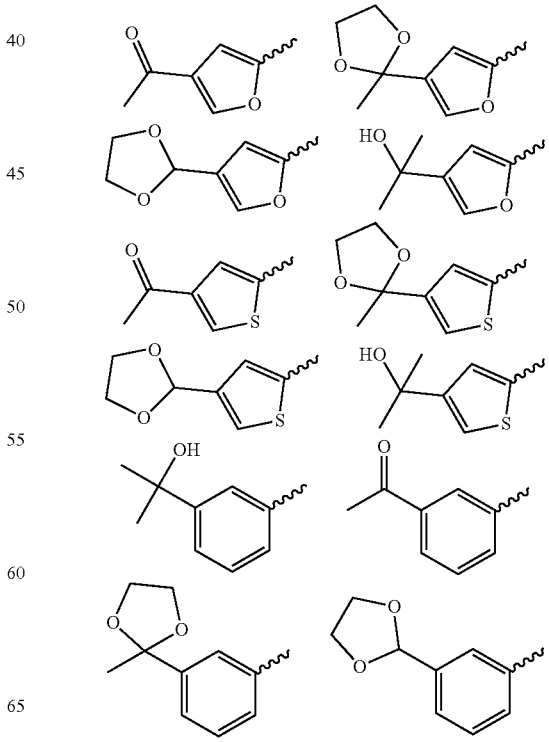

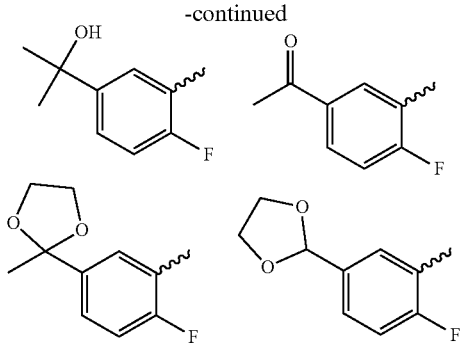

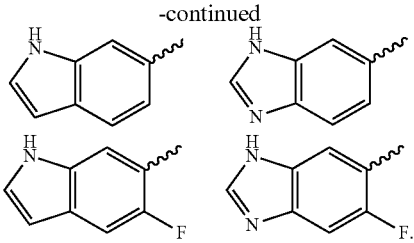

According to one preferred embodiment, the compound intended to be used according to the present invention is chosen from the following compounds:

| Compound number | Name | Structure |
|---|---|---|
| 1 | N-((4-chloro-2,6-diisopropylphenyl)carbamoyl)-3-(2-hydroxypropan-2-yl)benzenesulfonamide | 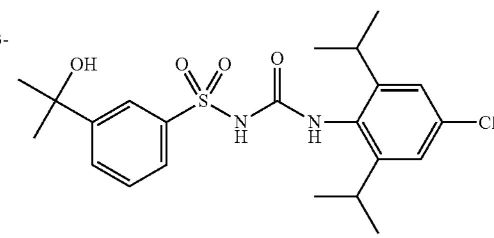 |
| 2 | N-((2,6-diisopropylphenyl)carbamoyl)-4-(2-hydroxypropan-2-yl)furan-2-sulfonamide | 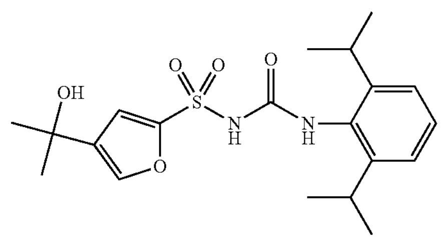 [SMILES: CC(C)c1cccc(C(C)C)c1NC(=O)NS(=O)(=O)c1cc(C(C)(C)O)co1] |
| 3 | N-((1,2,3,5,6,7-hexahydro-s-indacen-4-yl)carbamoyl)-4-(2-hydroxypropan-2-yl)furan-2-sulfonamide | 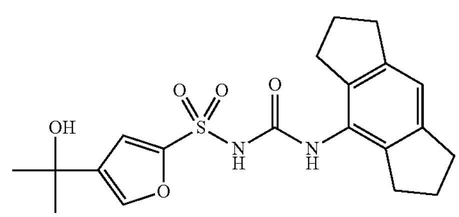 [SMILES: CC(C)(O)c1coc(S(=O)(=O)NC(=O)Nc2c3c(cc4c2CCC4)CCC3)c1] |
| 4 | 4-(1,3-dioxolan-2-yl)-N-((1,2,3,5,6,7-hexahydro-s-indacen-4-yl)carbamoyl)furan-2-sulfonamide | 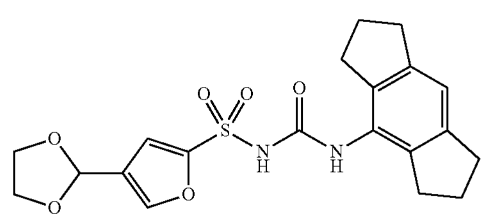 [SMILES: O=C(Nc1c2c(cc3c1CCC3)CCC2)NS(=O)(=O)c1cc(C2OCCO2)co1] |
| 5 | N-((1,2,3,5,6,7-hexahydrodicyclopenta[b,e]pyridin-8-yl)carbamoyl)-4-(2-hydroxypropan-2-yl)furan-2-sulfonamide | 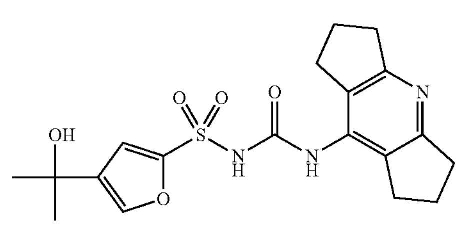 [SMILES: CC(C)(O)c1coc(S(=O)(=O)NC(=O)Nc2c3c(nc4c2CCC4)CCC3)c1] |

-continued

| Compound number | Name | Structure |
|---|---|---|
| 6 | N-((1,2,3,5,6,7-hexahydro-s-indacen-4-yl)carbamoyl)-4-(2-hydroxypropan-2-yl)thiophene-2-sulfonamide | 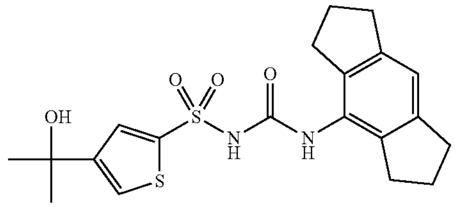 |
| 7 | N-((2,6-diisopropylphenyl)carbamoyl)-4-(2-hydroxypropan-2-yl)thiophene-2-sulfonamide | 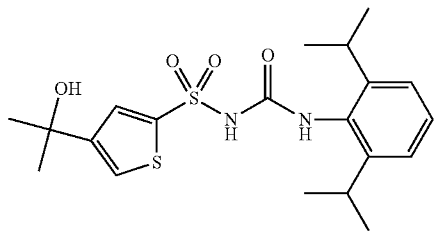 |
| 8 | 4-acetyl-N-((1,2,3,5,6,7-hexahydro-s-indacen-4-yl)carbamoyl)thiophene-2-sulfonamide | 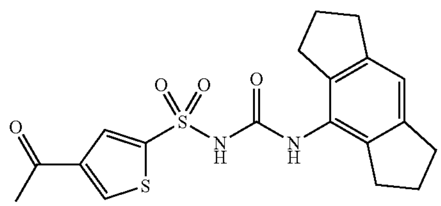 |
| 9 | N-((1,2,3,5,6,7-hexahydro-s-indacen-4-yl)carbamoyl)-1H-benzo[d]imidazole-5-sulfonamide | 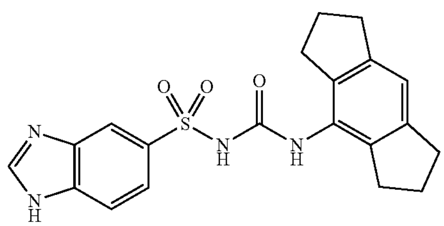 [SMILES: O=C(Nc1c2c(cc3c1CCC3)CCC2)NS(=O)(=O)c1ccc2[nH]cnc2c1] |
| 10 | N-((8-chloro-1,2,3,5,6,7-hexahydro-s-indacen-4-yl)carbamoyl)-4-(2-hydroxypropan-2-yl)furan-2-sulfonamide | 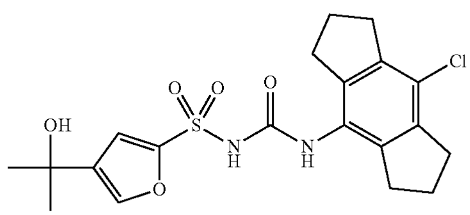 [SMILES: CC(C)(O)c1coc(S(=O)(=O)NC(=O)Nc2c3c(c(Cl)c4c2CCC4)CCC3)c1] |
| 11 | 4-acetyl-N-((1,2,3,5,6,7-hexahydro-s-indacen-4-yl)carbamoyl)furan-2-sulfonamide | 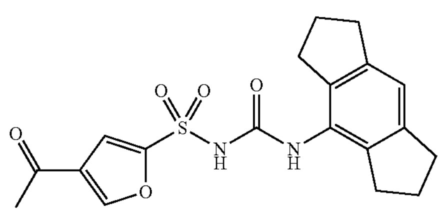 [SMILES: CC(=O)c1coc(S(=O)(=O)NC(=O)Nc2c3c(cc4c2CCC4)CCC3)c1] |
| 12 | N-((8-fluoro-1,2,3,5,6,7-hexahydro-s-indacen-4-yl)carbamoyl)-4-(2-hydroxypropan-2-yl)furan-2-sulfonamide | 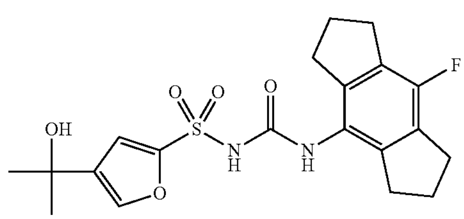 [SMILES: CC(C)(O)c1coc(S(=O)(=O)NC(=O)Nc2c3c(c(F)c4c2CCC4)CCC3)c1] |

-continued

| Compound number | Name | Structure |
|---|---|---|
| 13 | N-((4-fluoro-2,6-diisopropylphenyl)carbamoyl)-3-(2-hydroxypropan-2-yl)benzenesulfonamide | 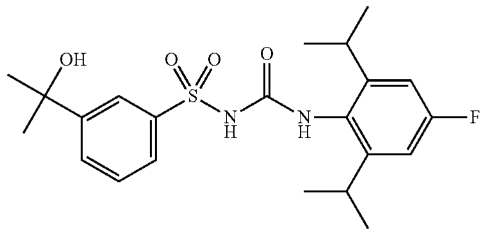 [SMILES: CC(C)c1cc(F)cc(C(C)C)c1NC(=O)NS(=O)(=O)c1cccc(C(C)(C)O)c1] |
| 14 | 6-fluoro-N-((1,2,3,5,6,7-hexahydro-s-indacen-4-yl)carbamoyl)-1H-benzo[d]imidazole-5-sulfonamide | 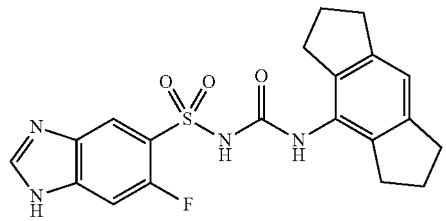 [SMILES: O=C(Nc1c2c(cc3c1CCC3)CCC2)NS(=O)(=O)c1cc2nc[nH]c2cc1F] |
| 15 | N-((4-chloro-2,6-diisopropylphenyl)carbamoyl)-1H-indole-6-sulfonamide | 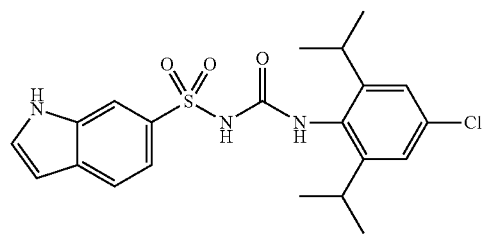 [SMILES: CC(C)c1cc(Cl)cc(C(C)C)c1NC(=O)NS(=O)(=O)c1ccc2cc[nH]c2c1] |
| 16 | N-((4-chloro-2,6-diisopropylphenyl)carbamoyl)-5-fluoro-1H-indole-6-sulfonamide | 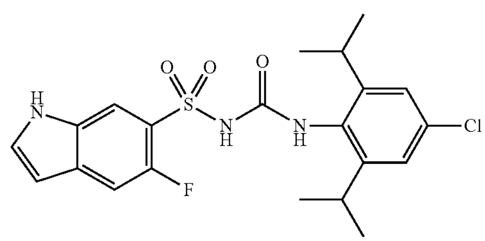 [SMILES: CC(C)c1cc(Cl)cc(C(C)C)c1NC(=O)NS(=O)(=O)c1cc2[nH]ccc2cc1F] |
| 17 | N-((1,2,3,5,6,7-hexahydro-s-indacen-4-yl)carbamoyl)-1H-indole-6-sulfonamide | 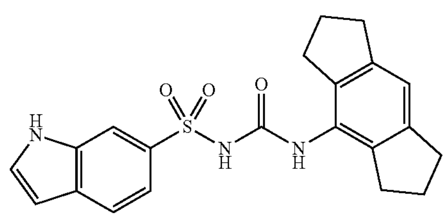 [SMILES: O=C(Nc1c2c(cc3c1CCC3)CCC2)NS(=O)(=O)c1ccc2cc[nH]c2c1] |
| 18 | 5-fluoro-N-((1,2,3,5,6,7-hexahydro-s-indacen-4-yl)carbamoyl)-1H-indole-6-sulfonamide | 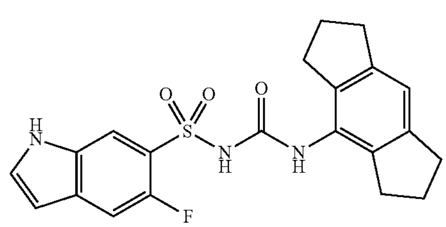 [SMILES: O=C(Nc1c2c(cc3c1CCC3)CCC2)NS(=O)(=O)c1cc2[nH]ccc2cc1F] |

| Compound number | Name | Structure |
|---|---|---|
| 19 | N-((4-chloro-2,6-diisopropylphenyl)carbamoyl)-2-fluoro-5-(2-methyl-1,3-dioxolan-2-yl)benzenesulfonamide | 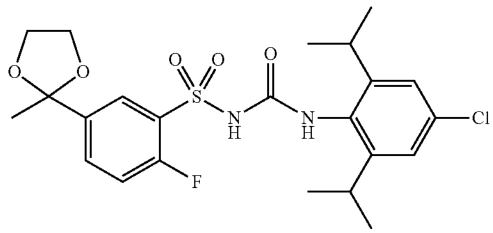 [SMILES: CC(C)c1cc(Cl)cc(C(C)C)c1NC(=O)NS(=O)(=O)c1cc(C2(C)OCCO2)ccc1F] |
| 20 | 2-fluoro-N-((1,2,3,5,6,7-hexahydro-s-indacen-4-yl)carbamoyl)-5-(2-methyl-1,3-dioxolan-2-yl)benzenesulfonamide | 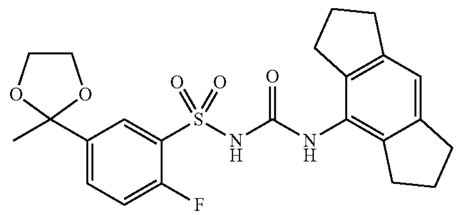 [SMILES: CC1(c2ccc(F)c(S(=O)(=O)NC(=O)Nc3c4c(cc5c3CCC5)CCC4)c2)OCCO1] |

In one preferred embodiment, the compound used is N-((1,2,3,5,6,7-hexahydro-s-indacen-4-yl)carbamoyl)-4-(2-hydroxypropan-2-yl)furan-2-sulfonamide.

These compounds and the methods for synthesizing them are clearly described in patent application WO 98/32733, in particular in the examples. Those skilled in the art may refer thereto for producing the compounds of general formula (I).

Pharmaceutical or Dermatological Compositions

The invention also relates to a pharmaceutical composition which can comprise at least one compound of general formula (I), or a pharmaceutically acceptable salt, solvate or hydrate thereof, intended to be used in the treatment and/or prevention of atopic dermatitis and/or of psoriasis.

In one preferred embodiment of the invention, the compound of general formula (I) and the pharmaceutical composition comprising a compound of general formula (I), or a pharmaceutically acceptable salt, solvate or hydrate thereof, are intended for topical administration.

In one alternative mode of the invention, the compound of general formula (I) and the pharmaceutical composition comprising a compound of general formula (I), or a pharmaceutically acceptable salt, solvate or hydrate thereof, are suitable for oral administration.

The compound of formula (I) can be used as an active ingredient. According to one particular aspect of the invention, at least one compound of general formula (I), or a pharmaceutically acceptable salt, solvate or hydrate thereof, can be used in combination with another active ingredient, for the treatment of an inflammatory skin disorder, and more particularly of atopic dermatitis and psoriasis.

The pharmaceutical and dermatological composition as described above can therefore contain inert additives, or even pharmacodynamically active additives, or combinations of these additives, and in particular:
wetting agents;
flavor improvers;
preservatives, such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal chelators;
depigmenting agents, such as hydroquinone, azelaic acid, caffeic acid or kojic acid;
emollients;
moisturizers, such as glycerol, PEG 400, thiamorpholinone, and its derivatives or urea;
non-steroidal anti-inflammatories;
carotenoids, and in particular β-carotene;
anti-psoriatic agents, such as anthraline and derivatives thereof;
eicosa-5,8,11,14-tetraynoic and eicosa-5,8,11-triynoic acids, and esters and amides thereof;
retinoids, i.e. RAR or RXR receptor ligands, which are natural or synthetic;
VDR receptor ligands;
corticosteroids or estrogens;
α-hydroxy acids and α-keto acids or derivatives thereof, such as lactic, malic, citric, glycolic, mandelic, tartaric, glyceric or ascorbic acids, and also salts, amides or esters thereof, or 3-hydroxy acids or derivatives thereof, such as salicylic acid, and also salts, amides or esters thereof;
ion channel, such as potassium channel, blockers;
or else, more particularly for the pharmaceutical compositions, in combination with medicaments known to interfere with the immune system (for example, cyclosporin, FK 506, glucocorticoids, monoclonal antibodies, soluble receptors, cytokines or growth factors, etc.).

Those skilled in the art will know how to select the optional compound(s) to be added to these compositions such that the desired effect is not, or not substantially, adversely affected by the addition envisioned.

Such a composition may be intended, and therefore suitable, for oral, topical, enteral, parental, ocular, sublingual, inhaled, subcutaneous, intramuscular, intravenous, transdermal, local or rectal administration. The compound of general formula (I), optionally in the form of a pharmaceutically acceptable salt, solvate and/or hydrate, alone or in combination with another active ingredient, can be administered in unit administration form, as a mixture with conventional pharmaceutical carriers or excipients, to animals and to human beings.

Preferably, the pharmaceutical composition is conditioned in a form that is suitable for topical administration.

The pharmaceutical composition comprising at least one compound of general formula (I) intended for use thereof according to the present invention is preferably formulated in a dermatological composition.

The composition of use according to the invention comprises a physiologically acceptable carrier or at least one pharmaceutically acceptable excipient, chosen according to the pharmaceutical, in particular dermatological, form desired and the method of administration chosen.

The terms "physiologically acceptable carrier" and "pharmaceutically acceptable excipient" are intended to mean respectively, for topical application, a carrier and an excipient which are compatible with the skin, the mucous membranes and the skin appendages.

Via the topical route, the pharmaceutical composition according to the invention is more particularly intended for treating the skin and mucous membranes, and may be in the form of ointments, creams, milks, pomades, powders, impregnated pads, syndets, solutions, gels, sprays, foams, suspensions, lotions, sticks, shampoos or washing bases. It may also be in the form of suspensions of lipid or polymeric microspheres, nanospheres or vesicles or polymer patches and hydrogels allowing a controlled release. This topical composition can be in anhydrous form, in aqueous form or in the form of an emulsion.

The compounds of general formula (I), or a salt, solvate or hydrate thereof, when it is administered topically, can in particular be used at a concentration generally of between 0.001% and 10% by weight, preferably between 0.01% and 5% by weight, relative to the total weight of the composition.

Therapeutic Applications

According to the present invention, the compounds described herein are used for the treatment and/or prevention of an inflammatory skin disorder, in particular of atopic dermatitis and/or psoriasis, preferably topically.

The compounds intended to be used according to the present invention by topical application have good skin penetration and good tolerance and a low toxicity with few or no side effects.

According to one preferred aspect of the invention, the preferred subjects for the treatment and/or the prevention of atopic dermatitis and/or of psoriasis are pregnant women, children and infants.

The composition of use according to the invention comprises at least one compound of general formula (I), or a pharmaceutically acceptable salt, solvate or hydrate thereof, in an amount sufficient to obtain the desired prophylactic or therapeutic effect. The useful dosage regimen varies according to age, sex and weight of the patient.

The compound of general formula (I), or a salt, solvate or hydrate thereof, can preferably be administered in a proportion of from 0.01 to 100 mg/kg and per day, advantageously from 0.01 to 50 mg/kg and per day. It is also possible to administer such doses in 2 to 4 daily administrations. Although these dosages are examples of average situations, there may be particular cases where higher or lower dosages are appropriate, such dosages are also part of the invention.

EXAMPLES

Example 1: Protocol for Testing an NLRP3 Antagonist (N-((1,2,3,5,6,7-hexahydro-s-indacen-4-yl)carbamoyl)-4-(2-hydroxypropan-2-yl)furan-2-sulfonamide, Compound 3, Also Known as MCC950) on a Mouse Atopic Dermatitis Model Female Balb/c mice were treated with the allergen *Dermatophagoides pteronyssinus* (DERP) in 3 cycles of epicutaneous sensitization (per patch) on the abdominal skin with 2 patches applied twice a week, followed by 2 weeks of rest, for 7 weeks. Topical treatments with an NLRP3 antagonist (compound 3, 2% in an acetone carrier) or a corticosteroid (0.1% betamethasone valerate, used as a control) were carried out 3 times over the course of the third and final week of sensitization (on days 44, 47 and 50).

An inflammatory reaction was induced by epicutaneous sensitization with patches impregnated with 100 μg of allergen in a sterile saline solution (*Dermatophagoides pteronyssinus* or DERP) or with a carrier applied to the abdominal skin 24 hours after shaving and left for three periods of 1 week (with a change of patch in the middle of the week), with a gap of 2 weeks between applications.

For the systemic route, the NLRP3 antagonist was administered intravenously, 200 μl, 2.5 mg/ml once a day, for the final series of epicutaneous sensitization with the allergen (D44 to D50).

For the topical administration, the test antagonist (compound 3) was formulated at 2% in an acetone carrier, applied to the sensitized skin 2 hours before the DERP patches were put in place. The topical treatments with an NLRP3 antagonist or a corticosteroid (used as a control) were carried out 3 times over the course of the third and final week of sensitization (on days 44, 47 and 50). At the time the final patch was removed (day 51), the skin and blood samples were collected.

Measurements

Insensible Water Loss (IWL) after Treatment with an NLRP3 Antagonist

The IWL is measured using a Tewameter on an animal the day before day 51. The Tewameter® probe measures the gradient of density of the evaporation of water from the skin indirectly by means of two sensors (temperature and relative humidity) inside a hollow cylinder. A microprocessor analyzes the values and expresses the evaporation rate in g/h/m$^2$.

Thickness of the Epidermis after Treatment with an NLRP3 Antagonist

The thickness of the epidermis is measured by histological morphometric analyses on sections 6 μm thick, stained with hematoxylin eosin (HE), originating from skin samples fixed beforehand in physiological saline.

Inflammatory Score after Treatment with an NLRP3 Antagonist

The inflammatory score is defined visually on the basis of predefined dryness, skin rash, baldness, excoriation and lichenification scales. The mean of the five scores given to one individual mouse on a given day indicates the clinical score given on the specific day.

Results

The results are shown in FIGS. 1 to 3. The topical and systemic NLRP3 antagonist made it possible to reduce all the parameters studied. The IWL, which is a clinical sign of skin barrier dysfunction, was significantly decreased (−60% for the systemic route and −42% for the topical route). Another skin barrier defect parameter, epidermal acanthosis, was partially restored with the NLRP3 antagonist (−38% for the systemic route and −24% for the topical route, over the thickness of the epidermis). The inflammatory parameters were also reduced, such as the inflammatory scores (−62% for the systemic route and −39% for the topical route). The efficacy of the NLRP3 antagonist tested is quite close to the treatment with corticosteroids, which are the reference treatments for atopic dermatitis.

Example 2: Protocol for Testing an NLRP3 Antagonist (N-((1,2,3,5,6,7-hexahydro-s-indacen-4-yl)carbamoyl)-4-(2-hydroxypropan-2-yl)furan-2-sulfonamide, Compound 3, Also Known as MCC950) on a Mouse Psoriasiform Model The treatment protocol consists of a daily topical application of Aldara® (3.18 mg of imiquimod) for 7 days to the shaved skin of Balb/c mice. The NLRP3 antagonist was dissolved in 3% acetone and was applied once a day 2 h before the treatment with Aldara®. The clinical score is an overall classification resulting from the sum of the erythema, edema and desquamation scores, on the basis of the overall evaluation by the physician of the Lattice system, known as LS PGA (J Am Acad Dermatol. 2004 October; 51(4):563-9).

The repeated topical application of imiquimod (IMQ) to the skin of the mice made it possible to demonstrate a reduction in the skin inflammation resembling the human psoriasis phenotype (PLoS One, 2011). Indeed, imiquimod induces inflamed scaly skin lesions resembling the psoriasis plaque. These lesions are associated with increased epidermal proliferation, abnormal differentiation, an epidermal accumulation of neutrophils in micro treatments, neoangiogenesis and infiltrates consisting of CD4+ T cells, of CD11c (+) dendritic cells and of plasmacytoid dendritic cells. Imiquimod induces an epidermal expression of IL-23, IL-17A and IL-17F, and also an increase in Th17 spleen cells.

The mice received a daily dose of 63.5 mg (14 μl) of commercially available imiquimod cream (5%) (Aldara®, 3M Pharmaceuticals) on the shaved skin of the back of mice for 7 consecutive days.

Results

In this model, the topical administration of the NLRP3 antagonist made it possible to reduce the skin inflammation induced by imiquimod (−36% on day 4 and −27% on day 5, on the basis of the clinical score, FIG. 4).

The invention claimed is:

1. A method for the treatment of a subject suffering from atopic dermatitis, comprising administering to the subject in need thereof an effective amount of a compound of formula (I), or a pharmaceutically acceptable salt, solvate or hydrate thereof:

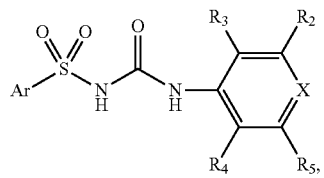

(I)

wherein:
X represents a group C—$R_1$ or a nitrogen atom;
$R_1$ represents a hydrogen atom or a halogen;
$R_2$, $R_3$, $R_4$ and $R_5$ independently represent a hydrogen atom or a $C_1$-$C_6$ alkyl, or $R_2$ and $R_3$ taken together can form a cyclopentyl with the carbon atoms of the phenyl to which they are bonded, or $R_4$ and $R_5$ taken together can form a cyclopentyl with the carbon atoms of the phenyl to which they are bonded; and
Ar represents a group selected from the group consisting of:

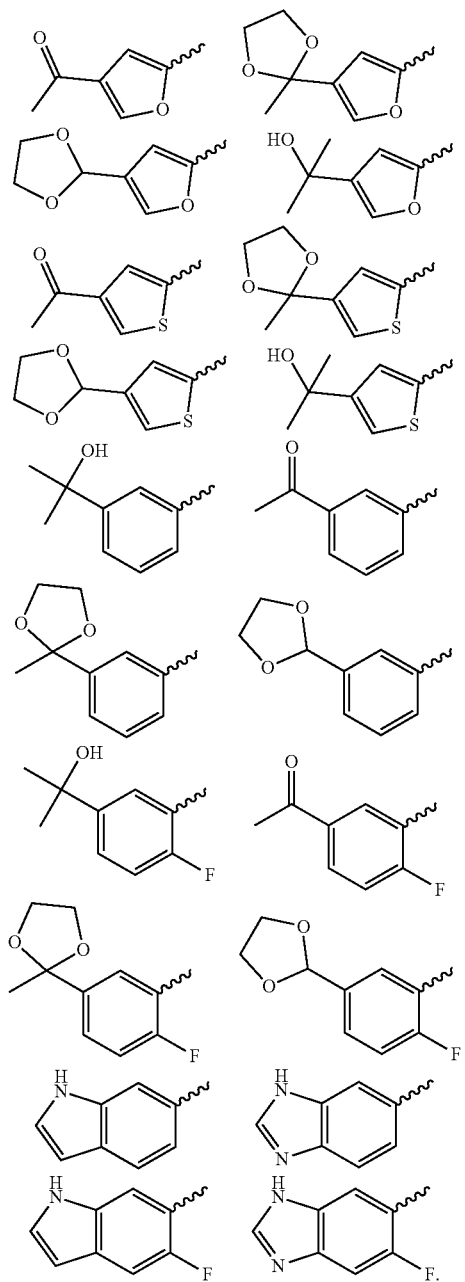

2. The method of claim 1, wherein:
X represents a group C—$R_1$ or a nitrogen atom, $R_1$ being as defined in claim 1;
$R_2$ and $R_3$ taken together forming a cyclopentyl with the carbon atoms of the phenyl to which they are bonded; and
$R_4$ and $R_5$ taken together can form a cyclopentyl with the carbon atoms of the phenyl to which they are bonded.

3. The method of claim 1, wherein:

X represents a group C—R$_1$ or a nitrogen atom, R$_1$ being as defined in claim 1;

R$_2$ and R$_5$ represent a hydrogen atom; and

R$_3$ and R$_4$ represent an isopropyl.

4. The method of claim 1, wherein the halogen is a chlorine or fluorine.

5. The method of claim 1, wherein the compound is selected from the group consisting of:

N-((4-chloro-2,6-diisopropylphenyl)carbamoyl)-3-(2-hydroxypropan-2-yl)benzenesulfonamide;

N-((2,6-diisopropylphenyl)carbamoyl)-4-(2-hydroxypropan-2-yl)furan-2-sulfonamide;

N-((1,2,3,5,6,7-hexahydro-s-indacen-4-yl)carbamoyl)-4-(2-hydroxypropan-2-yl)furan-2-sulfonamide;

4-(1,3-dioxolan-2-yl)-N-((1,2,3,5,6,7-hexahydro-s-indacen-4-yl)carbamoyl)furan-2-sulfonamide;

N-((1,2,3,5,6,7-hexahydrodicyclopenta[b,e]pyridin-8-yl)carbamoyl)-4-(2-hydroxypropan-2-yl)furan-2-sulfonamide;

N-((1,2,3,5,6,7-hexahydro-s-indacen-4-yl)carbamoyl)-4-(2-hydroxypropan-2-yl)thiophene-2-sulfonamide;

N-((2,6-diisopropylphenyl)carbamoyl)-4-(2-hydroxypropan-2-yl)thiophene-2-sulfonamide;

4-acetyl-N-((1,2,3,5,6,7-hexahydro-s-indacen-4-yl)carbamoyl)thiophene-2-sulfonamide;

N-((1,2,3,5,6,7-hexahydro-s-indacen-4-yl)carbamoyl)-1H-benzo[d]imidazole-5-sulfonamide;

N-((8-chloro-1,2,3,5,6,7-hexahydro-s-indacen-4-yl)carbamoyl)-4-(2-hydroxypropan-2-yl)furan-2-sulfonamide;

4-acetyl-N-((1,2,3,5,6,7-hexahydro-s-indacen-4-yl)carbamoyl)furan-2-sulfonamide;

N-((8-fluoro-1,2,3,5,6,7-hexahydro-s-indacen-4-yl)carbamoyl)-4-(2-hydroxypropan-2-yl)furan-2-sulfonamide;

N-((4-fluoro-2,6-diisopropylphenyl)carbamoyl)-3-(2-hydroxypropan-2-yl)benzenesulfonamide;

6-fluoro-N-((1,2,3,5,6,7-hexahydro-s-indacen-4-yl)carbamoyl)-1H-benzo[d]imidazole-5-sulfonamide;

N-((4-chloro-2,6-diisopropylphenyl)carbamoyl)-1H-indole-6-sulfonamide;

N-((4-chloro-2,6-diisopropylphenyl)carbamoyl)-5-fluoro-1H-indole-6-sulfonamide;

N-((1,2,3,5,6,7-hexahydro-s-indacen-4-yl)carbamoyl)-1H-indole-6-sulfonamide;

5-fluoro-N-((1,2,3,5,6,7-hexahydro-s-indacen-4-yl)carbamoyl)-1H-indole-6-sulfonamide;

N-((4-chloro-2,6-diisopropylphenyl)carbamoyl)-2-fluoro-5-(2-methyl-1,3-dioxolan-2-yl)benzenesulfonamide; and 2-fluoro-N-((1,2,3,5,6,7-hexahydro-s-indacen-4-yl)carbamoyl)-5-(2-methyl-1,3-dioxolan-2-yl)benzenesulfonamide;

or the pharmaceutically acceptable salt, solvate or hydrate thereof.

6. The method of claim 1, wherein the compound is N-((1,2,3,5,6,7-hexahydro-s-indacen-4-yl)carbamoyl)-4-(2-hydroxypropan-2-yl)furan-2-sulfonamide, or the pharmaceutically acceptable salt, solvate or hydrate thereof.

7. A method for the treatment of a subject suffering from atopic dermatitis, comprising administering to the subject in need thereof a pharmaceutical composition comprising an effective amount of a compound of formula (I), or a pharmaceutically acceptable salt, solvate or hydrate thereof:

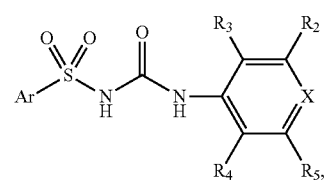

(I)

wherein:

X represents a group C—R$_1$ or a nitrogen atom;

R$_1$ represents a hydrogen atom or a halogen;

R$_2$, R$_3$, R$_4$ and R$_5$ independently represent a hydrogen atom or a C$_1$-C$_6$ alkyl, or R$_2$ and R$_3$ taken together can form a cyclopentyl with the carbon atoms of the phenyl to which they are bonded, or R$_4$ and R$_5$ taken together can form a cyclopentyl with the carbon atoms of the phenyl to which they are bonded; and Ar represents a group selected from the group consisting of:

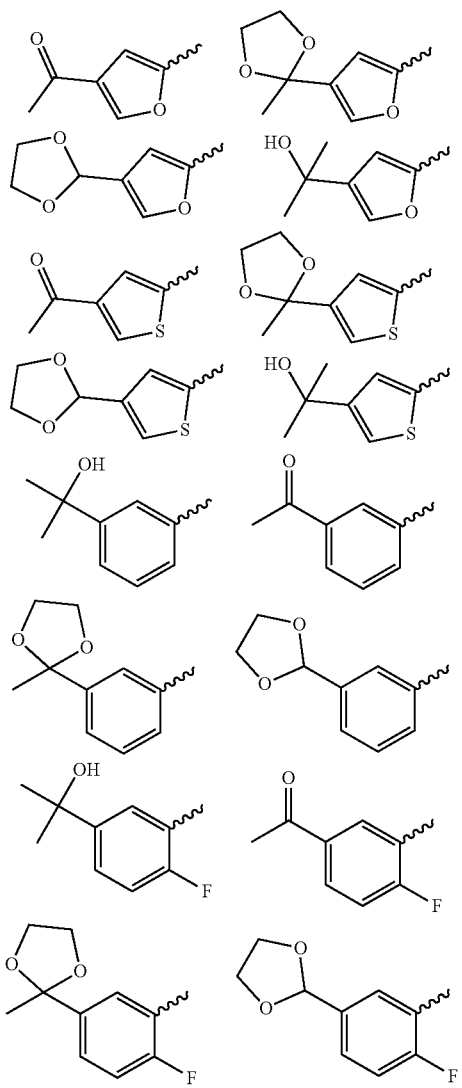

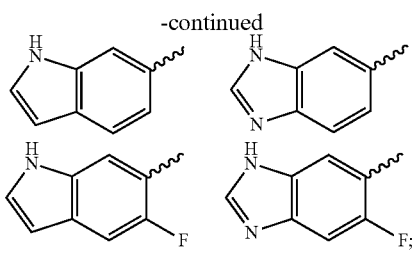

and a pharmaceutically acceptable carrier.

8. The method of claim 7, wherein:

X represents a group C—$R_1$ or a nitrogen atom, $R_1$ being as defined in claim 7;

$R_2$ and $R_3$ taken together forming a cyclopentyl with the carbon atoms of the phenyl to which they are bonded; and $R_4$ and $R_5$ taken together can form a cyclopentyl with the carbon atoms of the phenyl to which they are bonded.

9. The method of claim 7, wherein:

X represents a group C—$R_1$ or a nitrogen atom, $R_1$ being as defined in claim 7;

$R_2$ and $R_5$ represent a hydrogen atom; and $R_3$ and $R_4$ represent an isopropyl.

10. The method of claim 7, wherein the halogen is a chlorine or fluorine.

11. The method of claim 7, wherein the compound is selected from the group consisting of:

N-((4-chloro-2,6-diisopropylphenyl)carbamoyl)-3-(2-hydroxypropan-2-yl)benzenesulfonamide;

N-((2,6-diisopropylphenyl)carbamoyl)-4-(2-hydroxypropan-2-yl)furan-2-sulfonamide;

N-((1,2,3,5,6,7-hexahydro-s-indacen-4-yl)carbamoyl)-4-(2-hydroxypropan-2-yl)furan-2-sulfonamide;

4-(1,3-dioxolan-2-yl)-N-((1,2,3,5,6,7-hexahydro-s-indacen-4-yl)carbamoyl)furan-2-sulfonamide;

N-((1,2,3,5,6,7-hexahydrodicyclopenta[b,e]pyridin-8-yl)carbamoyl)-4-(2-hydroxypropan-2-yl)furan-2-sulfonamide;

N-((1,2,3,5,6,7-hexahydro-s-indacen-4-yl)carbamoyl)-4-(2-hydroxypropan-2-yl)thiophene-2-sulfonamide;

N-((2,6-diisopropylphenyl)carbamoyl)-4-(2-hydroxypropan-2-yl)thiophene-2-sulfonamide;

4-acetyl-N-((1,2,3,5,6,7-hexahydro-s-indacen-4-yl)carbamoyl)thiophene-2-sulfonamide;

N-((1,2,3,5,6,7-hexahydro-s-indacen-4-yl)carbamoyl)-1H-benzo[d]imidazole-5-sulfonamide;

N-((8-chloro-1,2,3,5,6,7-hexahydro-s-indacen-4-yl)carbamoyl)-4-(2-hydroxypropan-2-yl)furan-2-sulfonamide;

4-acetyl-N-((1,2,3,5,6,7-hexahydro-s-indacen-4-yl)carbamoyl)furan-2-sulfonamide;

N-((8-fluoro-1,2,3,5,6,7-hexahydro-s-indacen-4-yl)carbamoyl)-4-(2-hydroxypropan-2-yl)furan-2-sulfonamide;

N-((4-fluoro-2,6-diisopropylphenyl)carbamoyl)-3-(2-hydroxypropan-2-yl)benzenesulfonamide;

6-fluoro-N-((1,2,3,5,6,7-hexahydro-s-indacen-4-yl)carbamoyl)-1H-benzo[d]imidazole-5-sulfonamide;

N-((4-chloro-2,6-diisopropylphenyl)carbamoyl)-1H-indole-6-sulfonamide;

N-((4-chloro-2,6-diisopropylphenyl)carbamoyl)-5-fluoro-1H-indole-6-sulfonamide;

N-((1,2,3,5,6,7-hexahydro-s-indacen-4-yl)carbamoyl)-1H-indole-6-sulfonamide;

5-fluoro-N-((1,2,3,5,6,7-hexahydro-s-indacen-4-yl)carbamoyl)-1H-indole-6-sulfonamide;

N-((4-chloro-2,6-diisopropylphenyl)carbamoyl)-2-fluoro-5-(2-methyl-1,3-dioxolan-2-yl)benzenesulfonamide; and 2-fluoro-N-((1,2,3,5,6,7-hexahydro-s-indacen-4-yl)carbamoyl)-5-(2-methyl-1,3-dioxolan-2-yl)benzenesulfonamide;

or the pharmaceutically acceptable salt, solvate or hydrate thereof.

12. The method of claim 7, wherein the compound is N-((1,2,3,5,6,7-hexahydro-s-indacen-4-yl)carbamoyl)-4-(2-hydroxypropan-2-yl)furan-2-sulfonamide, or the pharmaceutically acceptable salt, solvate or hydrate thereof.

13. The method of claim 7, wherein the pharmaceutical composition is formulated for topical administration.

14. A method for the treatment of a subject suffering from atopic dermatitis and/or psoriasis, comprising administering to the subject in need thereof an effective amount of a compound of formula (I), or a pharmaceutically acceptable salt, solvate or hydrate thereof:

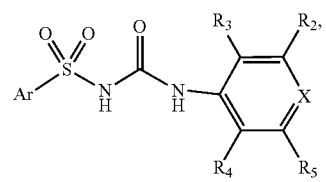

(I)

wherein:

X represents a group C—$R_1$ or a nitrogen atom;

$R_1$ represents a hydrogen atom or a halogen;

$R_2$, $R_3$, $R_4$ and $R_5$ independently represent a hydrogen atom or a $C_1$-$C_6$ alkyl, or $R_2$ and $R_3$ taken together can form a cyclopentyl with the carbon atoms of the phenyl to which they are bonded, or $R_4$ and $R_5$ taken together can form a cyclopentyl with the carbon atoms of the phenyl to which they are bonded; and Ar represents a group selected from the group consisting of:

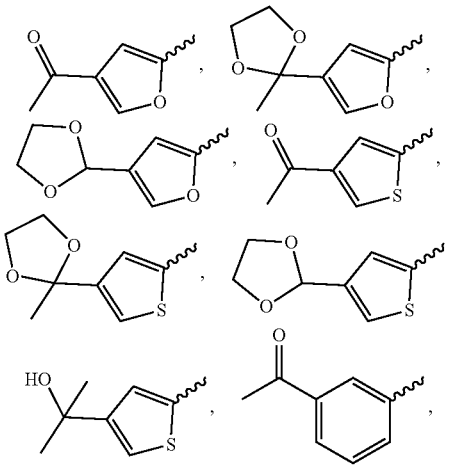

15. The method of claim 14, wherein:

X represents a group C—R₁ or a nitrogen atom, R₁ being as defined in claim 14;

R₂ and R₃ taken together forming a cyclopentyl with the carbon atoms of the phenyl to which they are bonded; and R₄ and R₅ taken together can form a cyclopentyl with the carbon atoms of the phenyl to which they are bonded.

16. The method of claim 14, wherein:

X represents a group C—R₁ or a nitrogen atom, R₁ being as defined in claim 14;

R₂ and R₅ represent a hydrogen atom; and

R₃ and R₄ represent an isopropyl.

17. The method of claim 14, wherein the halogen is a chlorine or fluorine.

18. The method of claim 14, wherein the compound is selected from the group consisting of:

4-(1,3-dioxolan-2-yl)-N-((1,2,3,5,6,7-hexahydro-s-indacen-4-yl)carbamoyl)furan-2-sulfonamide;

N-((1,2,3,5,6,7-hexahydro-s-indacen-4-yl)carbamoyl)-4-(2-hydroxypropan-2-yl)thiophene-2-sulfonamide;

N-((2,6-diisopropylphenyl)carbamoyl)-4-(2-hydroxypropan-2-yl)thiophene-2-sulfonamide;

4-acetyl-N-((1,2,3,5,6,7-hexahydro-s-indacen-4-yl)carbamoyl)thiophene-2-sulfonamide;

N-((1,2,3,5,6,7-hexahydro-s-indacen-4-yl)carbamoyl)-1H-benzo[d]imidazole-5-sulfonamide;

4-acetyl-N-((1,2,3,5,6,7-hexahydro-s-indacen-4-yl)carbamoyl)furan-2-sulfonamide;

6-fluoro-N-((1,2,3,5,6,7-hexahydro-s-indacen-4-yl)carbamoyl)-1H-benzo[d]imidazole-5-sulfonamide;

N-((4-chloro-2,6-diisopropylphenyl)carbamoyl)-1H-indole-6-sulfonamide;

N-((4-chloro-2,6-diisopropylphenyl)carbamoyl)-5-fluoro-1H-indole-6-sulfonamide;

N-((1,2,3,5,6,7-hexahydro-s-indacen-4-yl)carbamoyl)-1H-indole-6-sulfonamide;

5-fluoro-N-((1,2,3,5,6,7-hexahydro-s-indacen-4-yl)carbamoyl)-1H-indole-6-sulfonamide;

N-((4-chloro-2,6-diisopropylphenyl)carbamoyl)-2-fluoro-5-(2-methyl-1,3-dioxolan-2-yl)benzenesulfonamide; and 2-fluoro-N-((1,2,3,5,6,7-hexahydro-s-indacen-4-yl)carbamoyl)-5-(2-methyl-1,3-dioxolan-2-yl)benzenesulfonamide;

or the pharmaceutically acceptable salt, solvate or hydrate thereof.

* * * * *